US011529290B2

(12) United States Patent
Schulz et al.

(10) Patent No.: US 11,529,290 B2
(45) Date of Patent: Dec. 20, 2022

(54) MOBILE MEDICAL DRUG MANAGEMENT SYSTEMS AND METHODS

(71) Applicant: SIERRA NEVADA CORPORATION, Sparks, NV (US)

(72) Inventors: Karl Schulz, Sparks, NV (US); Richard Campbell, Sparks, NV (US); Emily Huang, Sparks, NV (US); Sarah Koh, Sparks, NV (US); Kurnhee Ma, Sparks, NV (US)

(73) Assignee: Sierra Nevada Corporation, Sparks, NV (US)

( * ) Notice: Subject to any disclaimer, the term of this patent is extended or adjusted under 35 U.S.C. 154(b) by 15 days.

(21) Appl. No.: 17/339,588

(22) Filed: Jun. 4, 2021

(65) Prior Publication Data

US 2021/0353504 A1  Nov. 18, 2021

Related U.S. Application Data

(63) Continuation of application No. 16/297,021, filed on Mar. 8, 2019, now Pat. No. 11,045,394.

(60) Provisional application No. 62/669,154, filed on May 9, 2018.

(51) Int. Cl.
| | |
|---|---|
| *B65D 83/04* | (2006.01) |
| *A61J 7/00* | (2006.01) |
| *G16H 40/40* | (2018.01) |
| *A61B 50/22* | (2016.01) |
| *A61K 31/485* | (2006.01) |
| *A61B 50/31* | (2016.01) |
| *G16H 10/60* | (2018.01) |
| *A61J 7/04* | (2006.01) |

(52) U.S. Cl.
CPC ............ *A61J 7/0069* (2013.01); *A61B 50/22* (2016.02); *A61K 31/485* (2013.01); *G16H 40/40* (2018.01); *A61B 50/31* (2016.02); *A61J 7/0076* (2013.01); *A61J 7/04* (2013.01); *G16H 10/60* (2018.01)

(58) Field of Classification Search
CPC .... A61J 1/16; A61J 7/04; A61J 7/0069; A61J 7/0076; A61B 50/22; A61B 50/31; A61K 31/385
USPC ............... 206/438, 534, 560, 565, 570, 571; 211/74
See application file for complete search history.

(56) References Cited

U.S. PATENT DOCUMENTS

| | | | |
|---|---|---|---|
| 1,520,444 A | 12/1924 | Romadka | |
| 2,159,904 A | 5/1939 | McDonough | |
| 2,740,516 A | 4/1956 | Renn | |
| 5,752,621 A | 5/1998 | Passamante | |
| 5,934,599 A | 8/1999 | Hammerslag | |
| 5,975,470 A | 11/1999 | Casey | |
| 6,123,205 A * | 9/2000 | Dumitrescu | B01L 9/06 211/74 |
| 7,048,130 B2 | 5/2006 | Hurst | |
| 7,434,686 B2 * | 10/2008 | Prindle | A61M 5/002 220/478 |
| 7,734,374 B2 | 6/2010 | Dallman | |

(Continued)

*Primary Examiner* — Luan K Bui
(74) *Attorney, Agent, or Firm* — Mintz Levin Cohn Ferris Glovsky and Popeo, P.C.

(57) ABSTRACT

Mobile systems and methods are adapted to control and document prehospital patient care reports and communication of patient status to a receiving medical treatment facility. The systems and methods relate to systems and methods for managing, recording, and administering drugs such as narcotics in an ambulatory and/or emergency environment.

18 Claims, 11 Drawing Sheets

(56) References Cited

U.S. PATENT DOCUMENTS

| | | | |
|---|---|---|---|
| 2002/0124905 A1* | 9/2002 | Draughn | A61J 1/16 |
| | | | 141/25 |
| 2003/0000864 A1 | 1/2003 | Carraro | |
| 2003/0083601 A1 | 5/2003 | Ballard et al. | |
| 2007/0090070 A1 | 4/2007 | Langham | |
| 2012/0246974 A1 | 10/2012 | Hammerslag et al. | |
| 2014/0117184 A1* | 5/2014 | Sharpe | B01L 9/06 |
| | | | 248/313 |
| 2015/0014492 A1* | 1/2015 | Sharpe | A61J 1/16 |
| | | | 248/312 |
| 2015/0164743 A1 | 6/2015 | Janson et al. | |
| 2015/0257976 A1* | 9/2015 | Puglisi | A61J 1/16 |
| | | | 206/216 |
| 2018/0183489 A1 | 6/2018 | Rasmussen | |
| 2018/0183656 A1 | 6/2018 | Jones | |
| 2019/0125472 A1* | 5/2019 | Lewis | A61B 50/31 |
| 2020/0268614 A1* | 8/2020 | Rivero | A61J 7/0481 |

* cited by examiner

MOBILE MEDICAL DRUG MANAGEMENT SYSTEMS AND METHODS

CROSS REFERENCE TO RELATED APPLICATIONS

This application is a continuation of U.S. application Ser. No. 16/297,021 filed on Mar. 8, 2019 and claims the benefit of U.S. Provisional Application No. 62/669,154 filed May 9, 2018, the contents of which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with Government support under W911W6-12-D0005, DO 0004. The Government has certain rights in the invention.

BACKGROUND

The present disclosure relates to documentation of prehospital patient care reports and communication of patient status to a receiving medical treatment facility. In current systems, ambulatory medical care providers, such as military medics, typically use pen and paper and/or an occasional radio call to a receiving medical treatment facility to report patient care data and status. This often results in inaccurate reporting of patient medical data.

For example, in the case of the administration of drugs to a patient, a military medic must often mentally do weight-based medical dosage math in guessing the patient's weight for proper dosage of drugs. Such medics are often required to do this math during high stress missions, usually with multiple trauma patients. This can often result in inaccurate dosages.

In addition, the medical care provider typically must write and/or maintain a log of narcotic use post-mission. The medical care provider may suffer penalties, such as job or pay loss, if the narcotics log is found to be inaccurate. Moreover, the medic care provider is typically issued pre-mission, loose drug vials in a hand-held case with a commercial off-the-shelf key lock to maintain drug security. During the mission, the medic must hold these very small vials in his/her hands and must often try to insert the needle in a very high vibration environment of either an air or ground MEDEVAC. Finger sticks, loss of drug vials, over/under-dosing of patients are common and unfortunate occurrences.

SUMMARY

In view of the foregoing, there is a need for improved systems and methods for documentation of prehospital patient care reports and communication of patient status to a receiving medical treatment facility particularly with respect to management of drugs such as narcotics. Disclosed are mobile systems and methods for documentation of prehospital patient care reports and communication of patient status to a receiving medical treatment facility. In one aspect of the disclosure, the systems and methods relate to systems and methods for managing, recording, and administering drugs such as narcotics in an ambulatory and/or emergency environment.

The systems and methods include a drug rack that includes various features for securely managing the administration of drugs. The drug rack is particularly suited for an environment outside of a hospital such as a pre-hospital environment. It can be used on military or emergency missions and is particularly suited for the harsh and unpredictable environments of such missions.

In an embodiment, the drug rack is communicatively and/or mechanically coupled to a weight-based drug calculator to assist in proper, weight-based dosage of drug by a medical provider. The rack also includes one or more mechanisms for securing the drugs pre/during/post mission for accountability and safer usability. This also adds safety measures to assist the care provider in selecting the proper drug during the mission. The system is also configured to maintain a log of the drugs pulled from the rack or otherwise manipulated for improved and accurate post-mission drug inventory. The system can also maintain an accurate and up-to-date patient health record.

In an embodiment, the drug rack includes one or more slots or seats that can contain standard-issue drug vials or containers, such as pain management, sedative, and paralytic vials (for example, 10 mL multi-dose, and 2 mL single-dose vials). The rack also includes a security mechanism, such as lock bar, to secure entry or access to the drug rack for mounting and unmounting the drug vials. The lock bar does not necessarily inhibit access to the vials for fluid withdrawal. As described below, the drug rack includes a primary security mechanism for medication withdrawal from the vials in the form of small access doors. Under normal use cases, these doors cannot be manually opened without gaining access via a software interface. Rather, the user must rely on an associated software interface to obtain access to the contents of the drug vials.

In addition, the rack includes one or more identifiers, such as light emitting diode (LED) indicators, that assist a medical care provider in identifying a proper drug for use with a patient. The drug rack may also include an electronic and/or mechanical access feature, such as one or more access doors, that automatically open to assist the medical care provider in accessing and identifying which drug vial was selected for administration on the patient. The access doors may automatically open when a corresponding drug is selected via a software user interface.

The system may include or otherwise be coupled to software that provides recommended dosages, and software buttons to open the access door(s) to the associated drug on the rack, which also illuminates an indicator light. The software buttons aid in the security of the drugs in that a user must have access to a user device, such as a tablet, and also be properly logged in as an authorized medic in order to activate the doors of the drug rack. In an example, an additional software button may be used to record the drug given and to also close the access door to the drug vial. The recorded drug's actual volume and dosage may be automatically captured during this process. The system may also be used scan the type of drug in the vial holder and to also automatically measure an amount of drug that was actually pulled from the vial. The system can also include wireless communication capabilities, such as for example, Bluetooth and Ultra-Wideband wireless connectivity to the drug rack and to a remote location.

More details of the devices, systems and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. The figures are not necessarily to scale in absolute terms or comparatively but are intended to be illustrative. Also, relative placement of features and elements may be modified for the purpose of illustrative clarity.

DETAILED DESCRIPTION

Disclosed are systems and methods for documentation of prehospital patient care reports and communication of patient status to a receiving medical treatment facility (i.e., a medical treatment facility that will receive a patient.) As mentioned, the system includes a drug rack that can be used to securely manage the storage, access, and distribution of drugs such as narcotics. The drug rack is portable and can be carried by a user, such as a medic, in connection with missions such as military and emergency missions.

Figure 1:
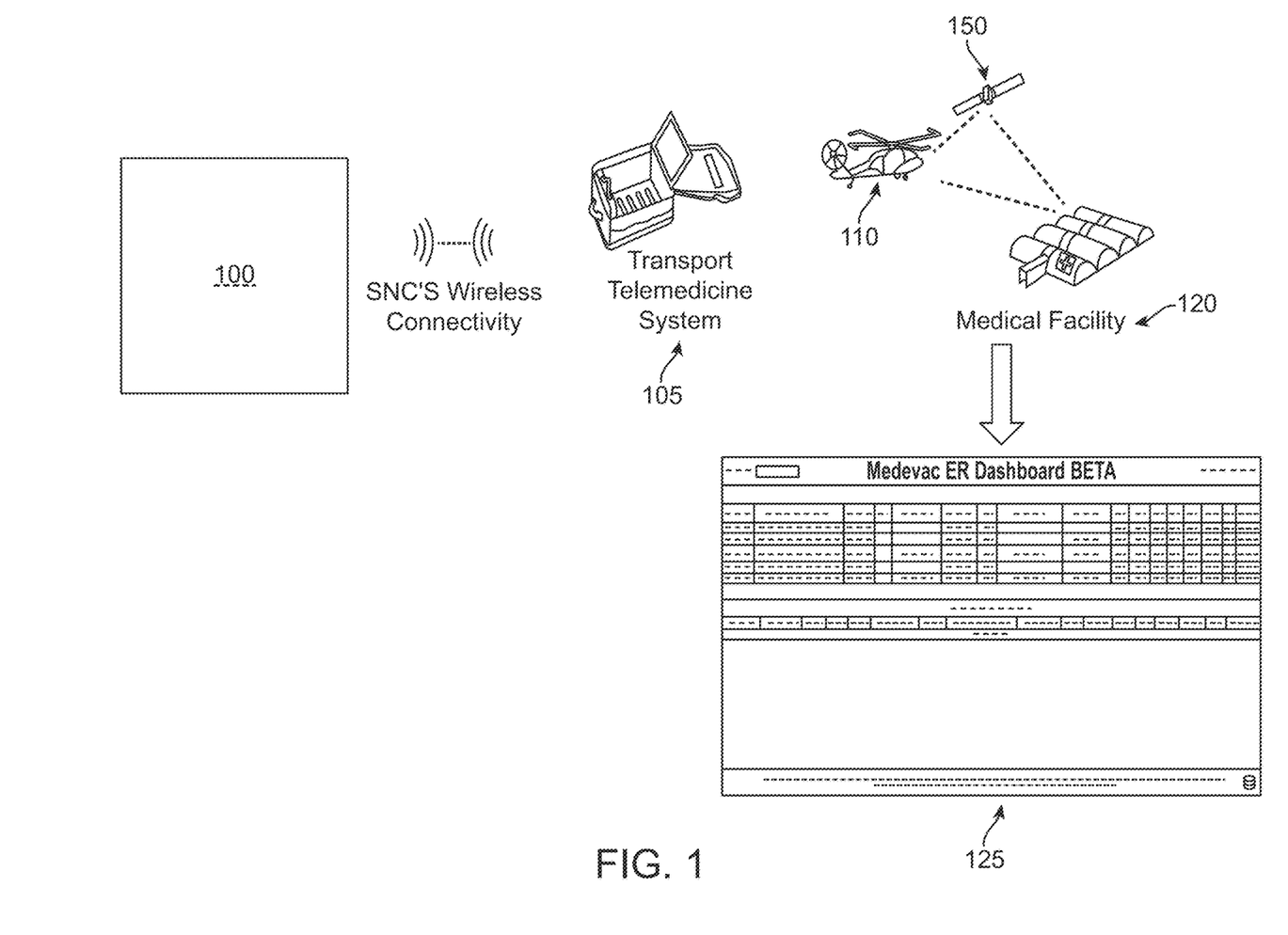
FIG. 1 shows a schematic representation of a system for documentation and management of prehospital patient care reports and communication of patient status to a receiving medical treatment facility.

FIG. 1 schematically shows an exemplary, high-level representation of a system for documentation and management of prehospital patient care reports and communication of patient status to a receiving medical facility 120. The system includes a mobile container system 105 (also referred to as a transport telemedicine system), which is described in more detail below with reference to FIG. 2. The mobile container system 105 is of a size such that it can be carried by a person, such as a medical care provider (e.g., a medic). The mobile container system 105 is also sized to be carried and transported in a mobile vehicle 110, such as a helicopter. The mobile container system 105 includes or can be coupled to a communication device, such as a wireless transmitter, that enables the mobile container system 105, to communicate with the medical facility 120, such as via communication with a satellite 150 and/or communication over a communication network such as the Internet.

In an example embodiment, the mobile container system 105 or any other component of the system is configured to communicate pursuant to the features described in the following U.S. patent applications, which are incorporated by reference in their entirety: (1) U.S. patent application Ser. No. 15/803,220 entitled "EXTENDED RANGE COMMUNICATIONS FOR ULTRA-WIDEBAND NETWORK NODES" and filed on Nov. 3, 2017; and (2) U.S. patent application Ser. No. 15/650,095 entitled "MULTI-BROKER MESSAGING AND TELEMEDICINE DATABASE REPLICATION" and filed on Jul. 14, 2017.

The system of FIG. 1 provides access to a user interface 125 that can provide user interaction with data collected by the mobile container system 105. Such interaction can include, for example, viewing the data as well as entering and modifying data. The user interface shown in FIG. 1 is a dashboard-like interface to be used by remote care providers to gain an overview of the condition and status of all patients associated with the mobile container system.

With reference still to FIG. 1, the mobile container system 105 is mechanically and/or wirelessly coupled to one or more devices 100, which can include a drug rack 305 (FIG. 3) that can be used to securely manage the storage, access, and distribution of drugs, as described in detail below.

The devices 100 can also include other types of devices, such as medical device that may be connected to the device mobile container system 105 either via a physical or wireless connection. The connected medical device(s) may include, for example, any number and combination of devices such as: EKG monitor, blood pressure monitor, heart rate monitor, ventilator, defibrillator, IV pump, EEG device, oxygen sensor, cardiovascular reserve index monitor or other similar devices.

The mobile container system 105 may be used at a point of care location, which can be any location where a care provider is providing medical care to a patient. In an embodiment, the point of care location is an emergency location such as a vehicle crash, battlefield or disaster site. Such environments may have limited communication capabilities that may adversely affect the ability to transmit data and may also have extreme environmental conditions. The point of care location may be any location that is remote from the point of care location. In an example, the remote location is at least more than several miles away from the medical facility 120.

Mobile Container System

Figure 2:
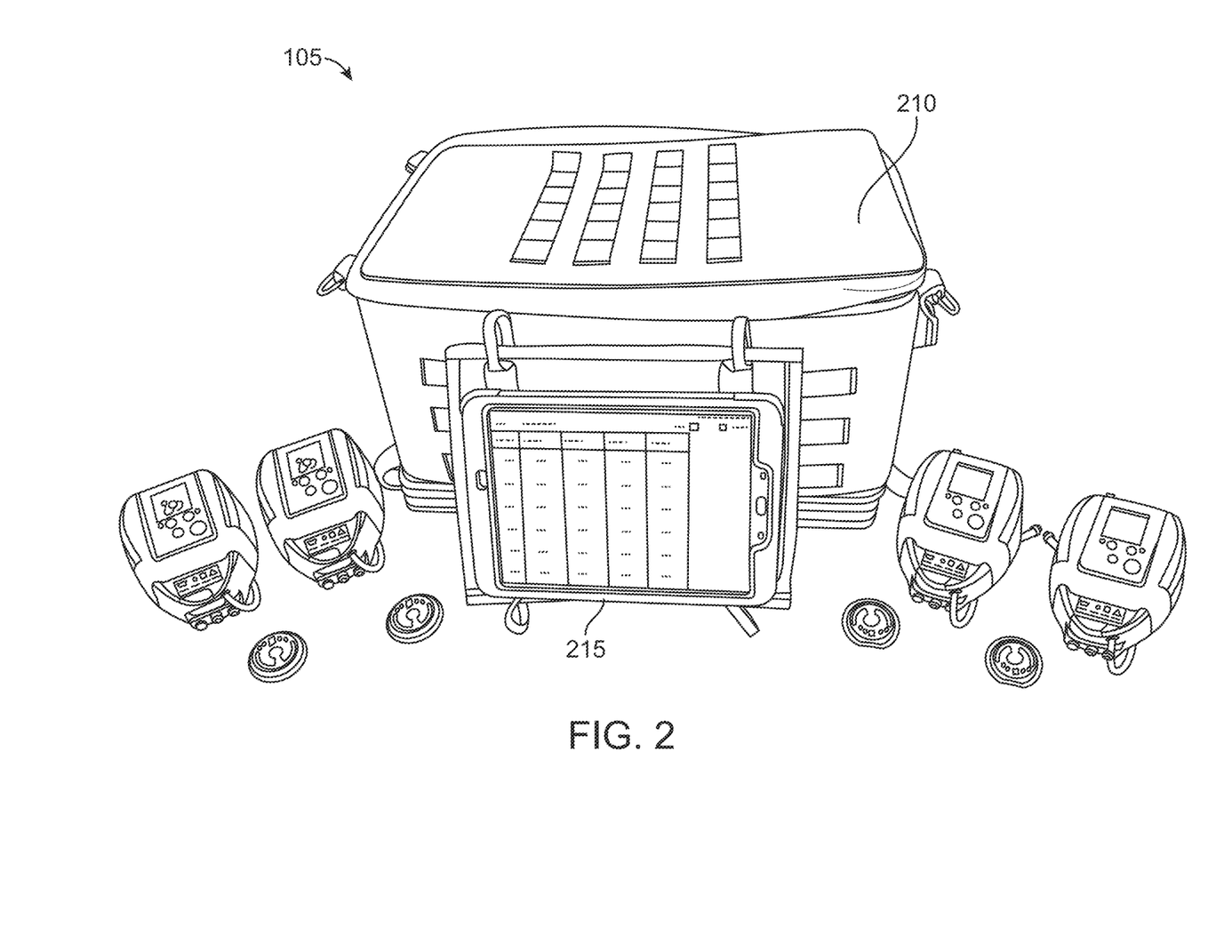
FIG. 2 shows a mobile container system that can be carried by a medical care provider for use in missions such as military and emergency missions outside of a hospital.

FIG. 2 shows the mobile container system 105, which includes a container 210 that can be carried by a medical care provider. The mobile container system 105 is communicatively coupled to a user device 215, which can be contained within or otherwise coupled to the container 210. The user device 215 can be any type of device that the care provider uses to enter, record, store, view and/or maintain data related to the care of the patient. The user device 215 may be, for example, a laptop computer, mobile phone, tablet, data pad, etc. The user device 215 generally includes a data input element such as a keypad and/or touch screen. In an embodiment, the device 215 includes voice recognition software that permits the user to verbally enter data into the device 215. In an embodiment, the user device 215 is held, controlled and/or operated by one or more transport personnel, such as a medic in an emergency environment. The user can input data into the user device 215 via a user interface. The user device 215 is configured to receive data from a user, wherein the data may relate to aspects of the patient, such as height, weight, blood pressure, or any data related to the patient.

FIG. 2 also shows other possible components such as an Athena GTX WVSM patient care device, which provides the following telemetric values: 3 lead ECG/EKG, Blood Pressure, SPO2 and heart rate. Another component can include a biomodule device, such as a Zephyr BioModule, which provides respiration rate, 2 lead ECG/EKG, and Accelerometer data.

As mentioned, a communication component may be coupled to the mobile container system 105. The communication component can be any device that is configured to transmit data to a remote location via a communication link, such as a line of sight, satellite or any other type of wireless communication link to the remote location. The communication link may include the Internet, public switched telephone network (PSTN), a private network, etc. The communication component may include any of a variety of communication devices that are configured to transmit data. For example, the communication component may include one or more antennas, modems, amplifiers, radios, or other types of transceivers, etc. The communication component enables the mobile container system 105 to transmit data from a database via wireless transmission (e.g., radio) to an external network in accordance with configured specifications, with the end user being another party such as a medical facility.

Drug Rack

Figure 3:
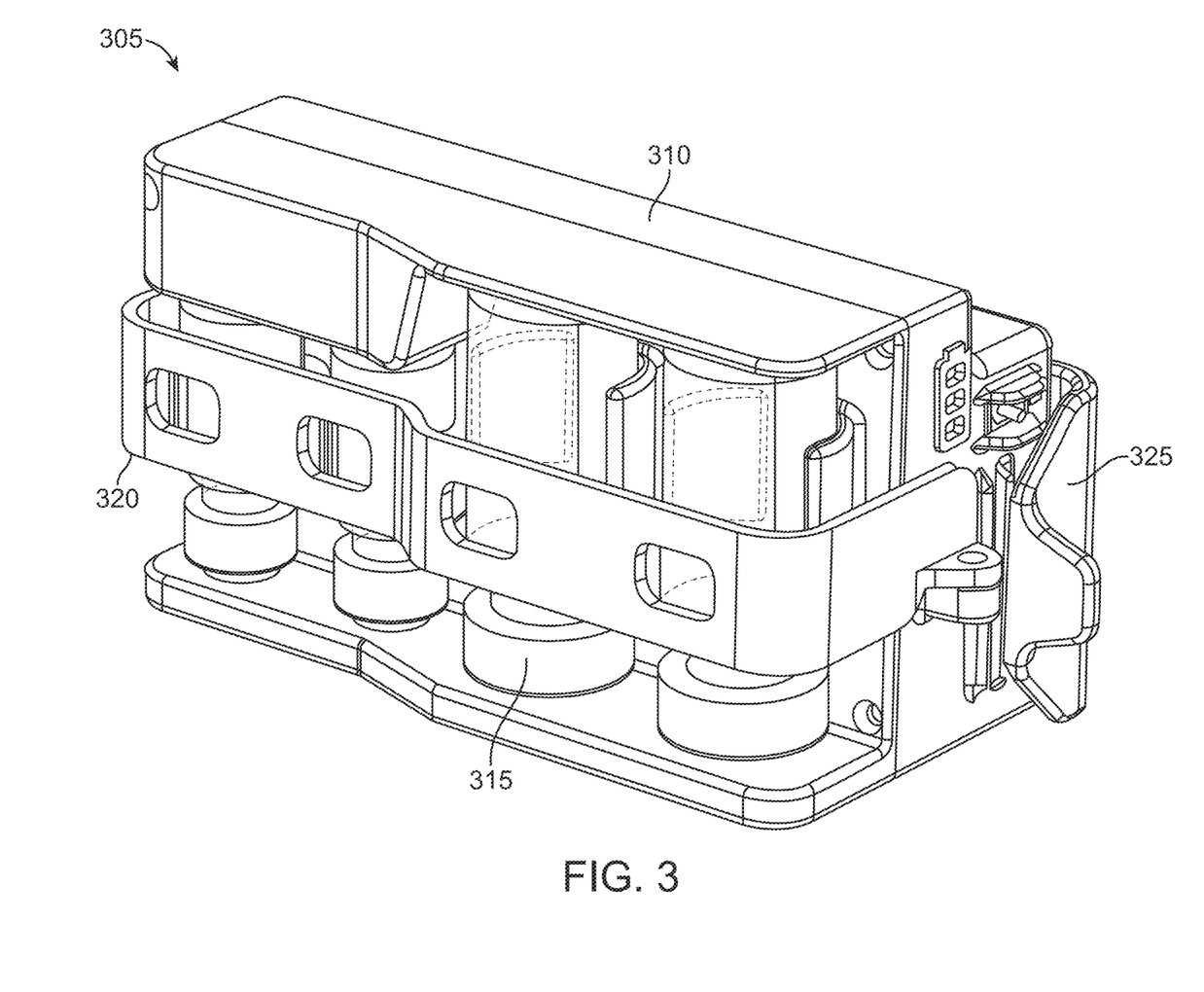
FIG. 3 shows a drug rack that can be coupled to the mobile container system.

As mentioned, the mobile container system 105 includes the drug rack 305, which is configured to manage the storage, access, and distribution of drugs. FIG. 3 shows a perspective view of an example embodiment of the drug rack 305. The drug rack 305 includes an outer housing 310 that is sized and shaped to contain and/or store one or more drug vials 315. The outer housing 305 can be any of a variety of shapes including the rectangular shape shown in FIG. 3. In a non-limiting example embodiment, the drug rack 305 has a size of 5 inches wide by 2.5 inches tall, by 2.5 inches deep and weighs no more than about 0.6 pounds. In another embodiment described below, the drug rack 305 is contained within or otherwise includes a housing with a lid that can be opened to exposed contents of the drug rack 305.

In the illustrated embodiment, the drug rack 305 is sized to contain four drug vials 315, which can be of equal or varying size relative to one another. In an example, the vials can be 10 mL multi-dose or 2 mL single-dose vials although the size of the vials can vary. It should be appreciated that the housing 310 can be sized to contain any quantity of vials although the preference is that the quantity be limited so that the housing is of a size than can be transported and/or easily carried by a user. In an example embodiment, the housing 310 contains no more than three, four, five, six, and up to ten vials although this may vary.

The housing 310 is configured such that it defines at least one slot or seat for each of the drug vials 315. The seats can be configured to receive therein a drug vial of various sizes, such as a large drug vial and a smaller drug vial. The drug vials 315 are arranged in one or more rows of drug vials as shown in FIG. 3 although the spatial arrangement of the drug vials can vary. A retaining member, such as a lock bar 320 is movably attached to the housing 310 such that, in a closed state, the lock bar 320, retains or secures the vials 315 within their respective seats in the housing 310. The lock bar 320 can move relative to the housing 310, such as in a pivoting or rotating manner, to an open state wherein the lock bar 320 does not impede or otherwise prevent the drug vials 315 from being removed from the housing 310. The lock bar 320 is positioned such that a vial, when seated in its seat, is interposed between the lock bar 320 and the seat so that the lock bar 320 prevents the vial from being removed from the seat when the lock bar is properly positioned.

The drug rack 305 can include a single lock bar 320 that collectively secures all the drug vials 315 as shown, or it can include a separate, dedicated lock bar for each of (or a subset of) the drug vials in the drug rack 305. The lock bar 320 can be lockingly secured in the closed state such as via a mechanical or electromechanical lock for security of the drugs contained within the drug rack 305.

Figure 4:
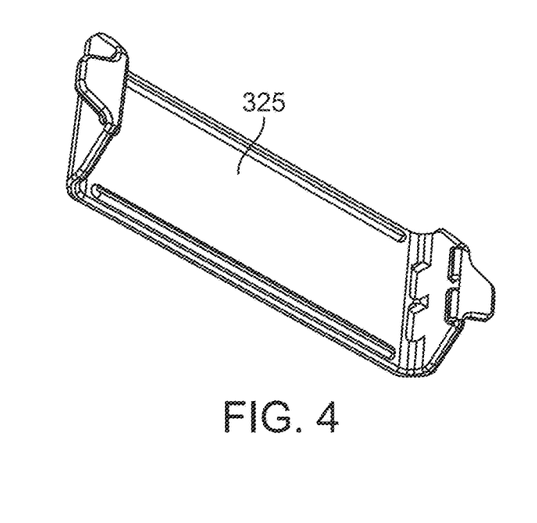
FIG. 4 shows a mounting clip for the drug rack of a mobile medication management system. The drug rack itself may also be referred to as a mobile medication management system or as a portion thereof.
Figure 5:
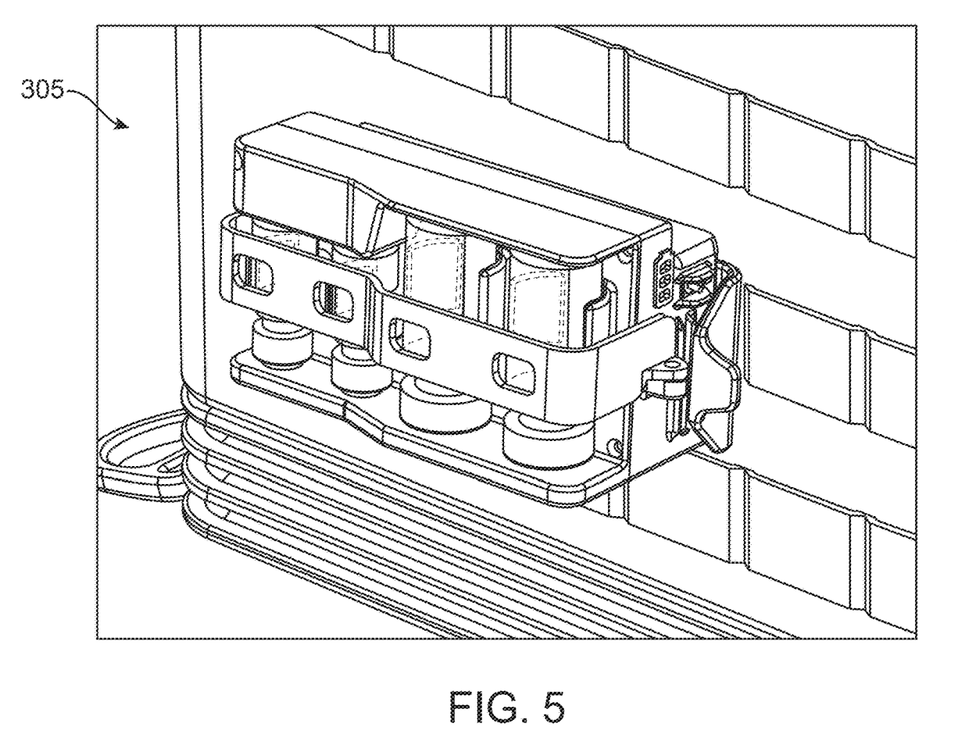
FIG. 5 shows the drug rack mounted to Modular Lightweight Load-carrying Equipment ("MOLLE").

With reference still to FIG. 3, the drug rack 305 can include a mounting clip 325 that is attached to the housing 310. The mounting clip 325 can be used to secure or otherwise mount the drug rack 305 to another object. FIG. 4 shows the mounting clip 325 and FIG. 5 shows the drug rack 305 mounted to a MOLLE as an example.

Figure 6:
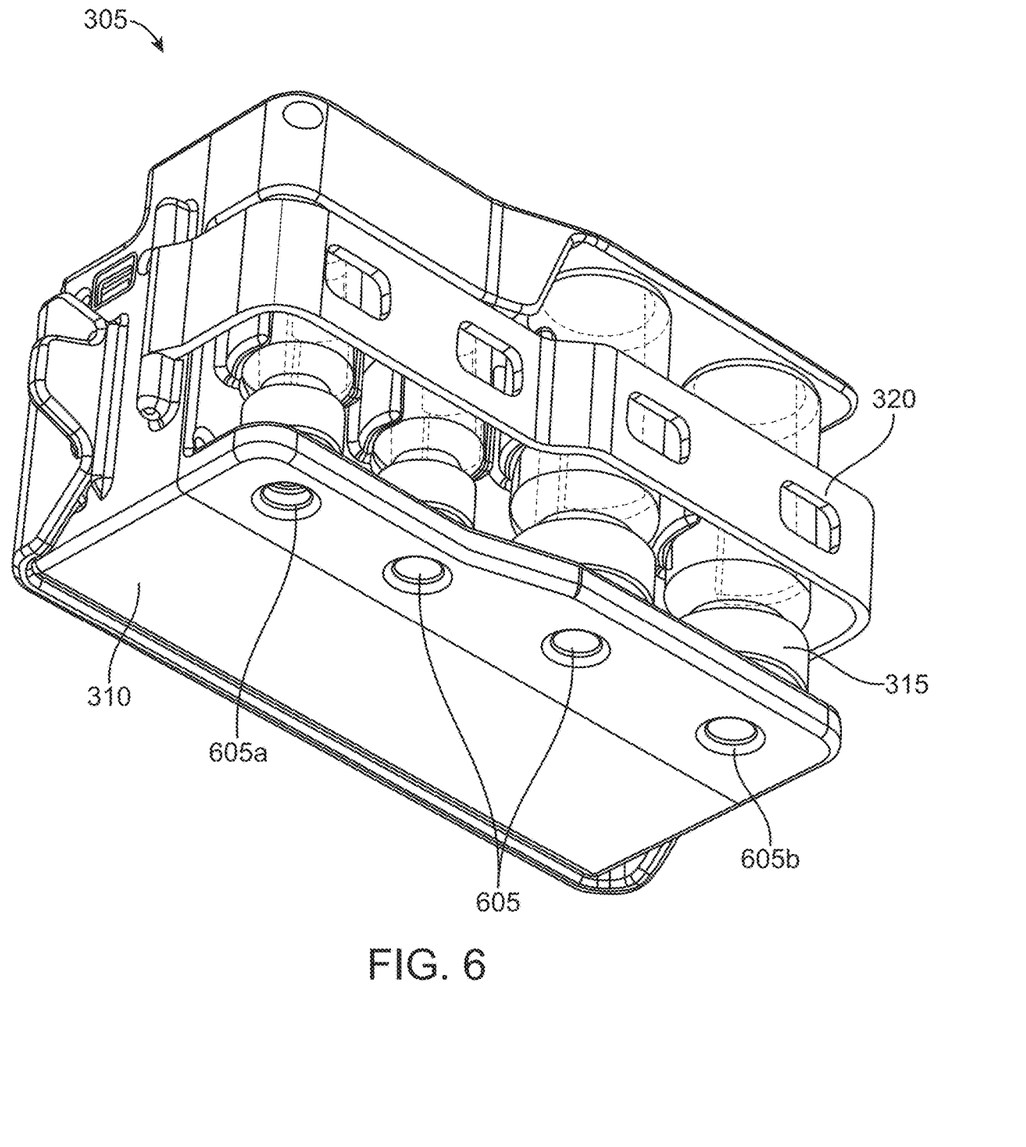
FIGS. 6 and 7 show bottom views of the drug rack.
Figure 7:
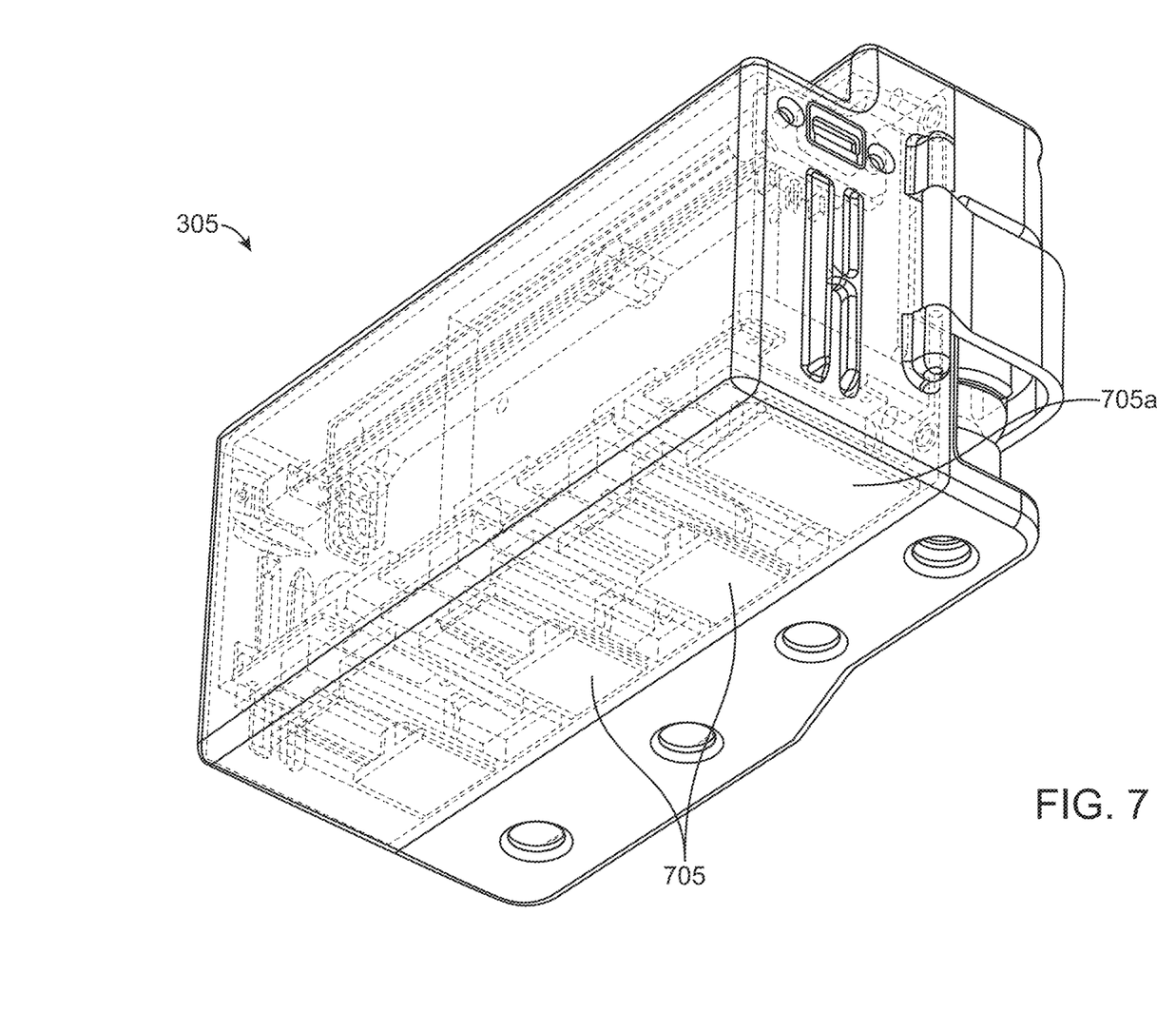

FIG. 6 shows a bottom view of the drug rack 305. FIG. 7 shows a bottom view with the drug rack being partially transparent so as to illustrate internal components of the drug rack. As shown in FIG. 6, an opening or port 605 is associated with each of the drug vials 315 at the bottom wall of the housing. Each port 605 provides an accessway by which a user, such as a medic, can access the contents of the respective drug vial 315. Each port 605 can transition between an open state and a closed state. Port 605a is shown in the open state while port 605b is shown in the closed state. When the port is in the open state, the contents of the respective drug vial are accessible by the user. When in the closed state, the contents of the respective drug vial are inaccessible by the user, as described below. The port(s) can include or be coupled to mechanical and/or electrical components, such as one or more electro-mechanical servo devices that enable control of the port(s).

The transparent view of FIG. 7 shows an example mechanism by which the ports 605 can transition between the open and closed states. Each port 605 has an associated door 705 that is movably positioned within the drug rack 305. Each door 705 can slidably transition between the closed state wherein the door 705 covers or otherwise blocks the respective port, and an open state wherein the door 705 does not cover or otherwise block the respective port. In FIG. 7, the door 705a is in the open state while the remainder of the doors 705 are in the closed state.

The drug rack 305 can include electromechanical components that are coupled to the doors 705 and the lock bar 320 for controlling these components between the open and closed states. The drug rack can also include software to automatically control these components, such as via interaction with a user and/or based upon satisfaction of predetermined conditions. In addition, the drug rack 305 can include features such a lights, sounds, and tactile feedback to provide the user with indications as to the availability of the drug, type of drug, dosage information for the drug, how much drug has been used, etc.

The drug rack can include, for example, one or more multi-color LED drug indicator lights that provide a color coded back light depending on the type of drug contained in the vials. For example, the lights can be color-coded such as Blue/Pain, Orange/Sedative, Purple/Paralytic.

Figure 8:
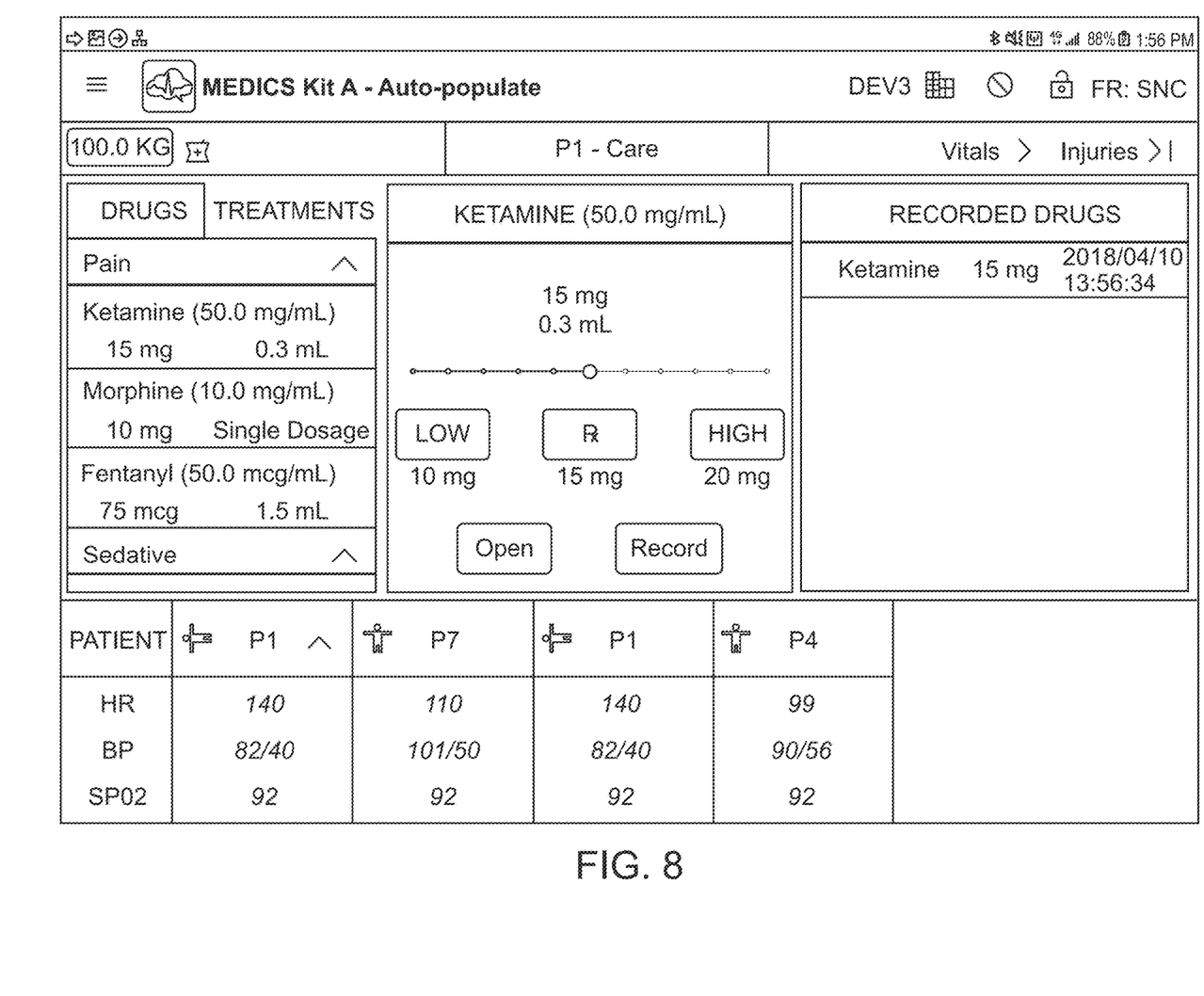
FIG. 8 shows an example user interface of the system.

The software can be coupled to a user interface, such as the example user interface shown in FIG. 8. The user interface can include data related to the drug vials and can also include features that enable the user to interact with the drug rack, such as to open/close/lock/unlock features of the drug rack. The access doors and/or the lock bar can be configured via software to automatically open after the care provider selects a drug to administer via the user interface. The software can also include a weight-based recommended drug calculator that can read weight automatically from a digital/wireless scale coupled to the system. The drug rack software can also automatically detect the drug type in a vial via a bar code scan and also the volume/dosage pulled from a vial.

Figure 9:
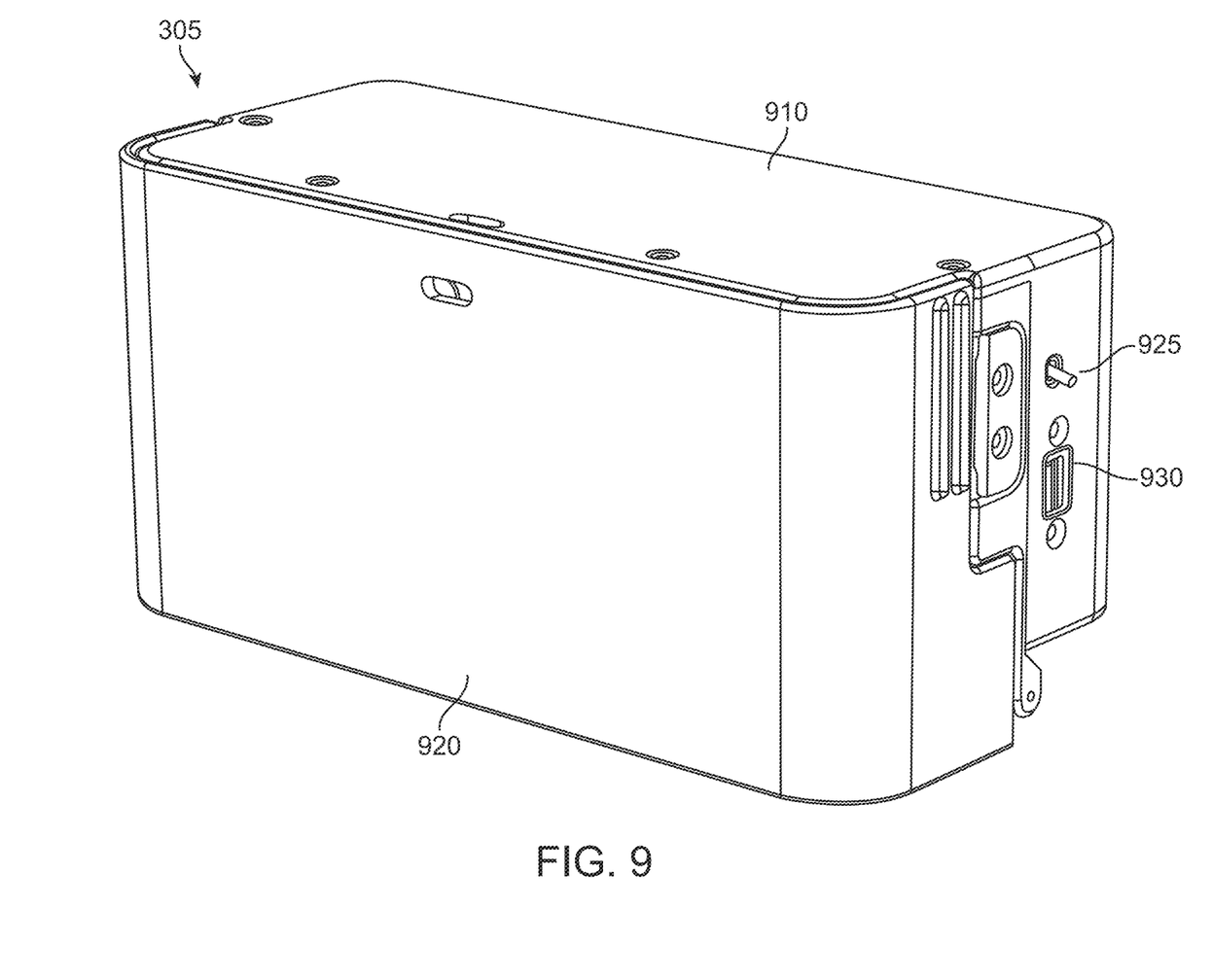
FIGS. 9 and 10 show perspective views of another embodiment of a drug rack.
Figure 10:
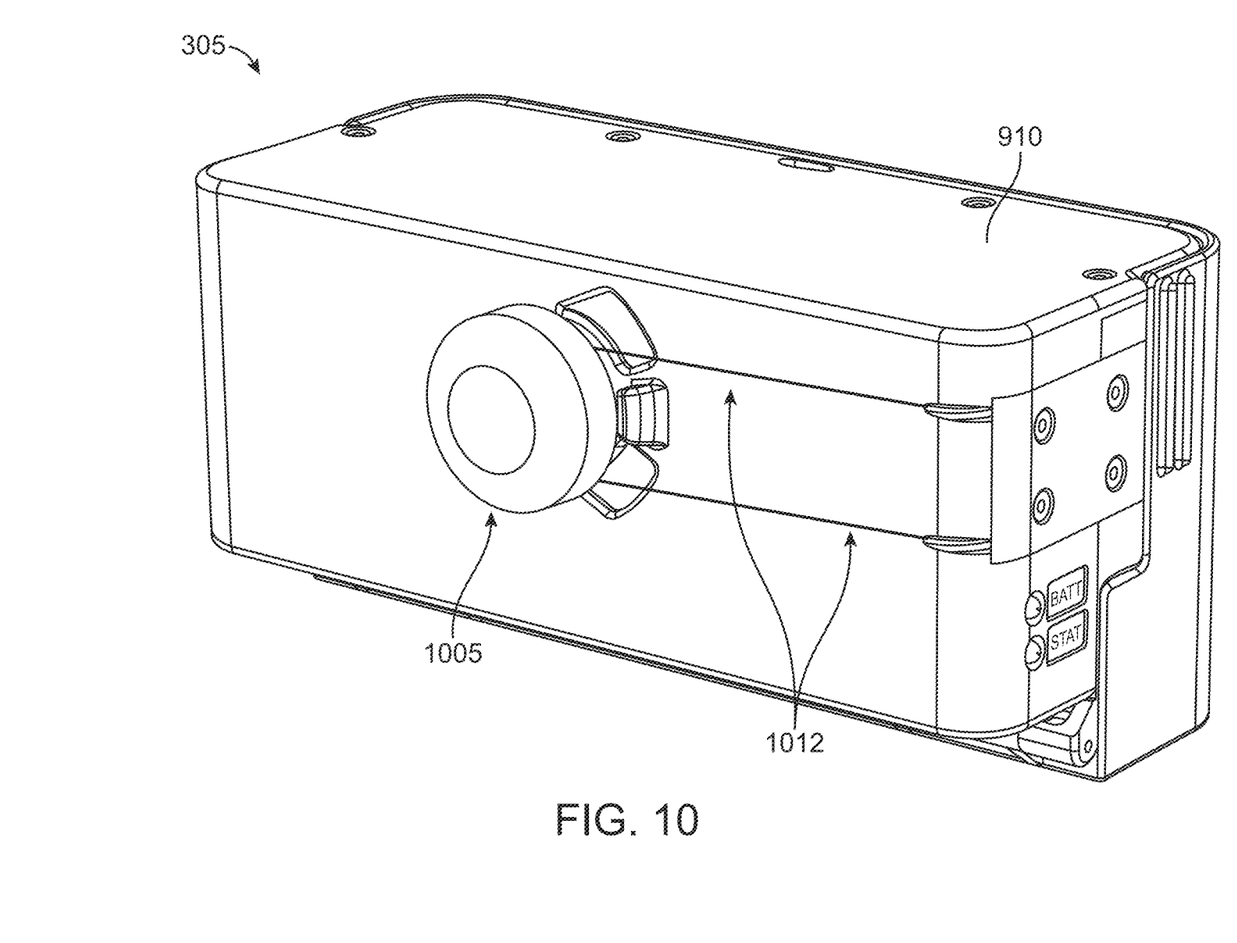

FIGS. 9 and 10 show perspective views of another embodiment of the drug rack 305. This embodiment includes an outer housing 910 with a movable lid 920 that transitions between an open and closed state. When in the closed state, the lid 920 covers the drug vials so as to prevent access to the drug vials. When in the open state, the lid does not cover the drug vials and does not prevent access to the drug vials. Rather, the lid provides a platform or surface that provides a location where a user can place instruments, such as needles, when accessing the drug vials. FIGS. 9 and 10 show the lid 920 in the closed state. In an example embodiment, the lid 920 is at least partially made of a transparent material such that a user can view the drug vials contained therein even when the lid is closed. As shown in FIG. 9, the drug rack 305 can include components such as a power (or "on/off") switch 925. The drug rack 305 can also include a port 930, such as a USB port, for charging the drug rack and or coupling a USB device to the drug rack 305.

As shown in FIG. 9, the outer housing 910 and lid 920 can include an interface such as a pair of holes through which a tie element can be inserted and tied for locking the lid closed. The outer housing 910 can also include other components such as magnets for securing the lid 920 in the closed state.

As shown in FIG. 10, the drug rack 305 can include a tightening mechanism 1005 that a user can actuate to tighten and to also release tension on one or more elongated members such as cables or wires 1012 (or other actuation component) that individually or collectively serve as a retaining member or locking element for vials contained within the drug rack 305, as described more fully below. The wires 1012 wrap around vials contained within the drug rack 305 and can be tightened to lockingly secure the vials within the drug rack 305. In an embodiment, the tightening mechanism includes a ratcheting device that can be actuated, such as via rotation or other movement, to place the wires in tension and/or release the wires from tension. In a non-limiting example, the ratcheting device includes a rotatable knob.

Figure 11:
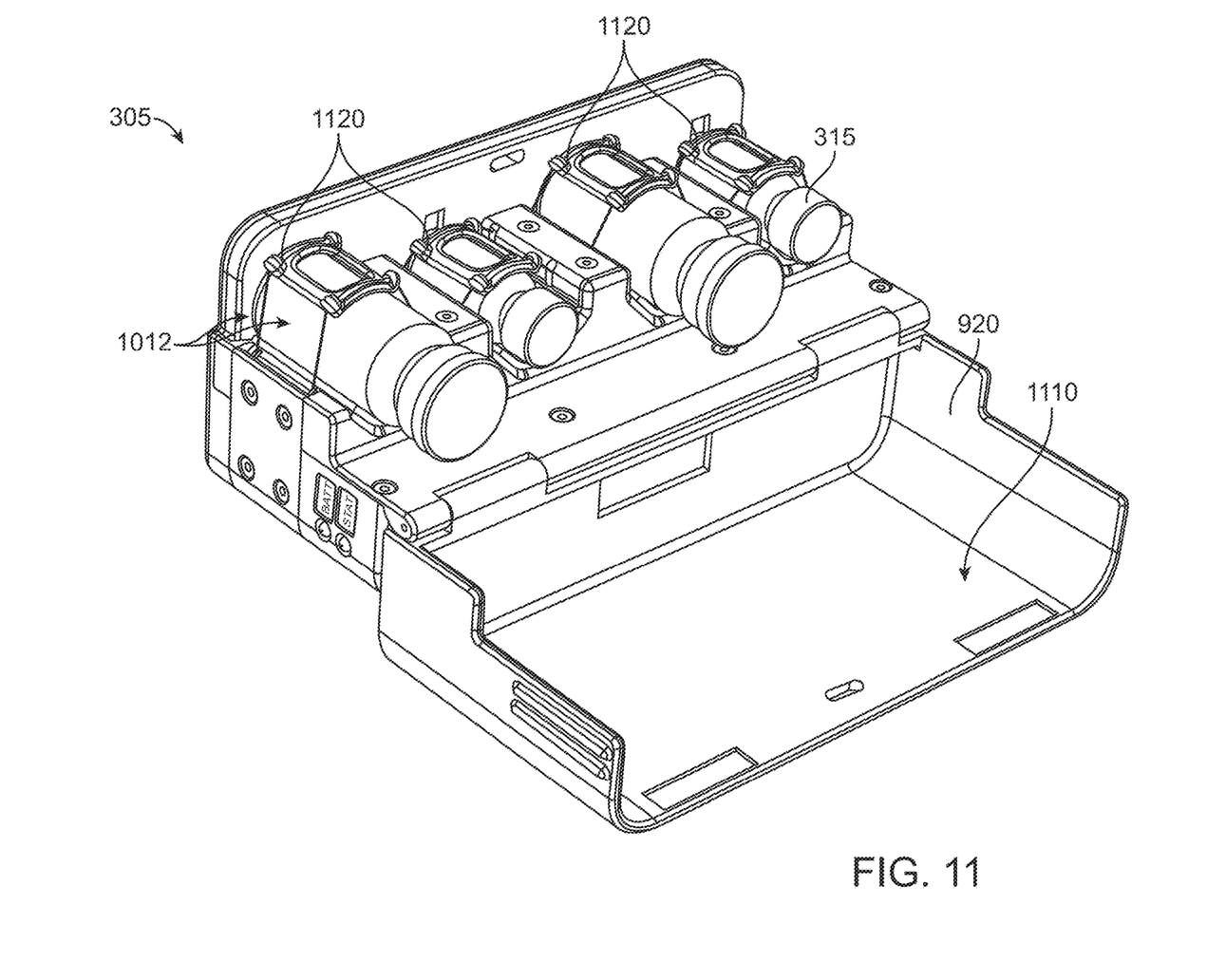
FIGS. 11 and 12 show the drug rack of FIGS. 9 and 10 with a lid in an open state.

FIG. 11 shows the drug rack 305 with the lid 920 in the open state wherein the lid is open relative to the outer housing 910 so as to expose the vials 315. In FIG. 11, the drug rack 305 is in an example orientation in which a user, such as a medic, can use the drug rack 305. The lid 920 is coupled to the outer housing 910 via one or more hinges 1105 that enable the lid 920 to rotate between the open state and the closed state. It should be appreciated that other mechanisms aside from rotatable hinges can be used to enable the transition of the lid between the open and closed states.

The lid 920 defines a flat or substantially flat, horizontal platform or surface 1110 that defines a space where a user, such as a medic, can rest his or her hands as the vials are being accessed. The surface 1110 also provides a platform upon which the user can also place one or more items, such as a needle. The flat surface 1110 aids in the medic inserting a needle into a vial such as during a high vibration environment. The lid 920 and/or the outer housing 910 can include one or more securing elements, such as magnets, to maintain the lid 920 in an open or closed state. The vials 315 are positioned relative to the surface 1110 such that ends of the vials 315 are facing and immediately adjacent to the surface 1110. That is, an open or access portion (such as where a needle can be inserted) of the vial 315 is immediately adjacent the surface 1110, such as abutting and/or contacting the surface or within an inch or two of the surfaces. This permits the user to easily access both the surface 1110 and the vials 315.

As mentioned with respect to the prior embodiment, each vial 315 is seated within a corresponding slot or seat. When seated as such, the drug rack 305 orients each vial 315 so that a top portion or access portion of the vial is presented to a user for convenient access. The seat can be shaped to correspond or complement the shape of the vial so that the vial can sit flush within the respective seat. Each vial has a corresponding saddle 1120 that abuts, grabs, or otherwise stabilizes or the vial when seated in its seat. The saddle 1120 can be tightened about its respective vial to lock the vial within its seat. The saddle 1120 can be made of a material that is flexible or malleable such that the saddle can conform to the shape of the respective vial when the saddle is tightened over the vial.

As mentioned, the saddles 1120 can be tightened about their respective vials to lock the vials within their seats. In this regard, the wires 1012 (FIGS. 10 and 11) are threaded through the saddles and also threaded through at least a portion of the drug rack so as to secure the drug vials 315 relative to the drug rack. The wires 1012 can be placed in tension to exert a force that constrains the saddles 1120 and their respective vials in place within their seats. The actuator 1005 (FIG. 10) can be used to tighten and release the tension on the wires 1012. In a non-limiting embodiment, the actuator 1005 is part of a tightening mechanism, such as the tightening mechanism described in U.S. Pat. No. 5,934,599, which is incorporated herein by reference in its entirety.

Figure 12:
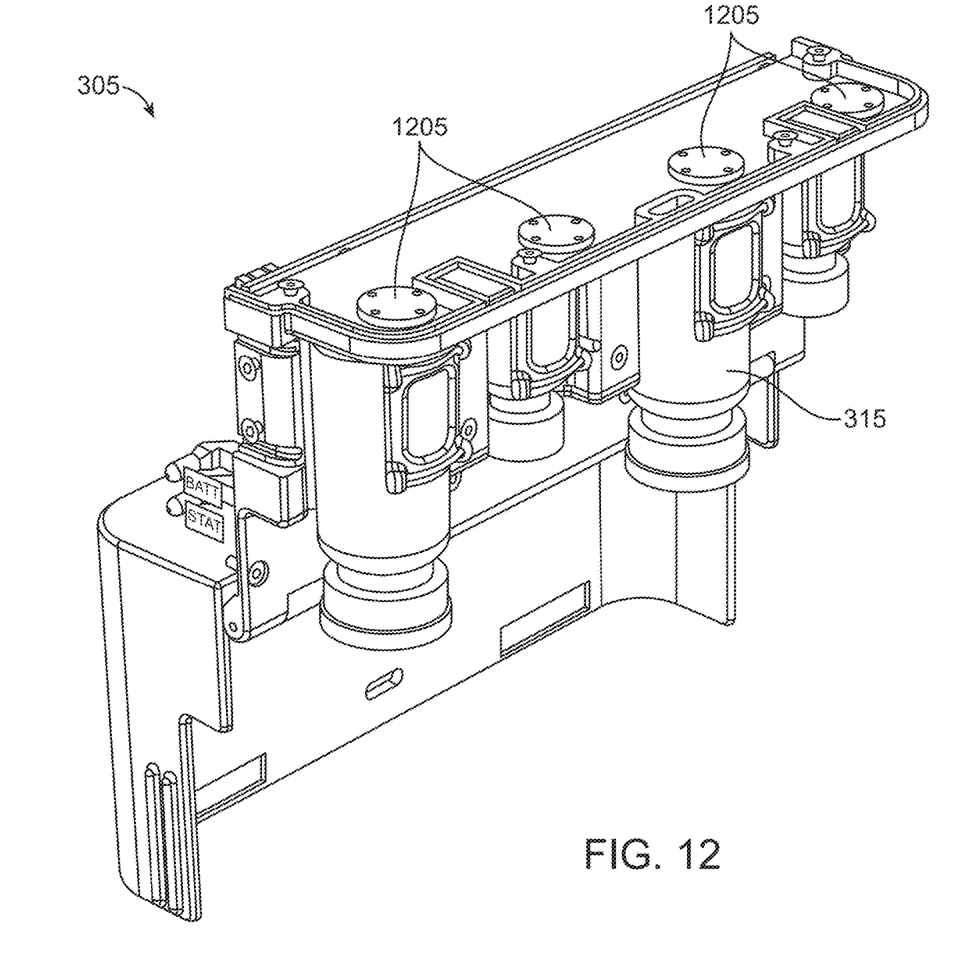

FIG. 12 shows another view of the drug rack 305. The lid and a portion of the outer housing are not shown in FIG. 12 for clarity of illustration. As mentioned, the drug rack 305 can include one or more multi-color LED drug indicator lights that provide a color coded back light depending on the type of drug contained in the vials. As shown in FIG. 12, the one or more LEDs 1205 can be located on the drug rack 305 at or near a bottom region of each vial 315. When illuminated, an LED emits light through a clear bottom region of the drug vial. The light refracts in the material of the vial (such as glass) and within the material inside the vial (such as liquid) so as to make the vial glow. The drug rack can include infrared capabilities and/or night vision capabilities that utilize infrared LEDs for illumination of the vial(s).

In a method of use, a user, such an emergency medic, is transported via a mobile vehicle 110 to a location that requires medical treatment for a patient. The location can be an emergency location such as a disaster site or a battle site. The user can carry the mobile container system 105 or a portion thereof during transport or can also mount the mobile container system 105 on the vehicle. Upon reaching a location, the user can carry the mobile container system 105 or a portion thereof on his or her body without assistance from a transport device such as a cart. The user can then treat a patient by accessing the user interface. The user can gain access to the contents of one or more drug vials of the drug rack via interaction with the user interface, which may request credentials or other security access requirements. Upon accessing the content(s) of the drug vial(s), the mobile container system 105 can locally or remotely records or otherwise memorialize data related to the drug or contents accessed via the vial. For example, the system can record, via the drug rack, that a specific drug was administered at a certain time, the time the drug was given, the name or other data related to the patient, the dosage amount, etc.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example would a non-transient solid-state memory or a magnetic hard drive or any equivalent storage medium. The machine-readable medium can alternatively or additionally store such machine instructions in a transient manner, such as for example as would a processor cache or other random-access memory associated with one or more physical processor cores.

To provide for interaction with a user, the subject matter described herein can be implemented on a device having a display device, such as for example a liquid crystal display (LCD) monitor for displaying information to the user and a keyboard and a input device, such as for example a mouse or a trackball, by which the user may provide input to the device. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

The invention claimed is:

1. A handheld drug rack system, comprising:
 a housing defining at least one seat sized to receive therein a drug vial, wherein the housing is sized to be held by a user;
 a retaining member coupled to the housing and positioned such that a vial, when seated in the at least one seat, is interposed between the retaining member and the at least one seat so that the retaining member secures the vial within the at least one seat, wherein the retaining member comprises at least one elongated member formed of a wire that at least partially wraps the drug vial, and wherein the retaining member is mechanically coupled to a tightening mechanism that can be actuated to place the at least one wire in tension, and wherein the tightening mechanism comprises an actuator that can be rotated to place the at least one elongated member in tension; and
 at least one port in the housing, wherein the at least one port provides an accessway by which a user can access the contents of a respective drug vial.

2. The drug rack system of claim 1, wherein the at least one seat includes a plurality of seats, and wherein each seat in the plurality of seats is sized to receive a drug vial.

3. The drug rack system of claim 1, wherein each seat is sized to contain a vial of various sizes.

4. The drug rack system of claim 1, further comprising a door that covers the port to prevent access of the at least one drug vial.

5. The drug rack system of claim 4, wherein the door can movably transition between a closed state wherein the door covers or otherwise blocks the port, and an open state wherein the door does not cover or otherwise block the port.

6. The drug rack system of claim 5, wherein the door slidably transitions between the closed state and the open state.

7. The drug rack of claim 5, further comprising an electromechanical component coupled to the door and configured to movably transition the door between the closed state and the open state.

8. The drug rack system of claim 1, wherein the drug rack is coupled to software that controls the drug rack.

9. The drug rack system of claim 8, wherein the software controls transition of the door between the closed state and the open state.

10. The drug rack system of claim 1, further comprising a lid movable attached to the housing.

11. The drug rack system of claim 10, wherein the lid transitions between a closed state and an open state.

12. The drug rack system of claim 11, wherein the lid, when in the open state, defines a horizontal platform.

13. The drug rack system of claim 12, wherein the horizontal platform is positioned immediately adjacent the vial.

14. The drug rack system of claim 1, wherein the port is coupled to a mechanical-electrical servo to control access to a respective vial.

15. The drug rack system of claim 1, wherein the actuator includes a ratcheting device.

16. The drug rack system of claim 1, wherein drug rack is configured to record data related to access of a drug vial.

17. The drug rack system of claim 16, wherein the data includes a time that a vial is accessed and a name of a patient.

18. The drug rack system of claim 1, further comprising a saddle coupled to the at least one seat, wherein the saddle abuts a vial when the vial is seated in the at least one seat, wherein the saddle is flexible such that the saddle can conform to the shape of a vial when the saddle is tightened over the vial, and wherein the at least one elongated member is threaded through the saddle.

* * * * *